United States Patent [19]

Johnsen et al.

[11] 4,280,808
[45] Jul. 28, 1981

[54] ENDODONTIC FILE HOLDER

[75] Inventors: James B. Johnsen; Hal J. Oien, both of Portland, Oreg.

[73] Assignee: Jordco, Inc., Portland, Oreg.

[21] Appl. No.: 147,379

[22] Filed: May 6, 1980

[51] Int. Cl.³ .............................................. A61C 1/14
[52] U.S. Cl. ...................................... 433/77; 433/141
[58] Field of Search ..................... 433/102, 81, 72, 25, 433/77

[56] References Cited

U.S. PATENT DOCUMENTS

| 902,109 | 10/1908 | Powell | 433/49 |
| 3,949,568 | 4/1976 | Gallagher | 63/1 A |

FOREIGN PATENT DOCUMENTS

| 672565 | 10/1937 | Fed. Rep. of Germany | 433/102 |
| 819512 | 10/1937 | France | 63/1 R |

*Primary Examiner*—Robert Peshock
*Attorney, Agent, or Firm*—Kolisch, Hartwell & Dickinson

[57] ABSTRACT

Ring-like apparatus for use in handling endodontic files. The apparatus includes a socket member forming a tapered socket having a larger upper end and a smaller lower end. A deformable tapered cushion is receivable in the socket, with a portion of the cushion projecting through the socket's lower end. When such portion is pulled downwardly and then released, it bulges against the socket member, at the socket's lower end, forming a bulge which holds the cushion releasably in the socket. Files may be embedded releasably in the opposite (upper) end of the cushion. The apparatus includes a band enabling wearing of the apparatus on a user's finger. A trough arrangement formed in the apparatus, cooperating with a calibration scale, allows the user to adjust, with his free hand, the position of a file depth marker slidably held on a file's shaft.

6 Claims, 9 Drawing Figures

ENDODONTIC FILE HOLDER

BACKGROUND AND SUMMARY

The present invention relates to endodontic apparatus, and more particularly, to hand-holdable devices for containing and depth-setting endodontic files.

In endodontic therapy, a drainage cavity is drilled to a selected depth in a tooth. The depth of the cavity is gauged, at periodic intervals during drilling, by inserting into the cavity an endodontic file having a depth marker which is set at a preselected position on the file's shaft.

In conventional endodontic practice, a dental assistant holds a file dispenser from which the dentist can withdraw fresh endodontic files, and into which he can place used files. A risk associated with this practice is that the dentist or assistant may be pierced by a file in transferring the same, with the liklihood of serious infection resulting. Also, the assistant is poorly utilized in such practice.

It is one very general object of the present invention to provide an endodontic file holder which overcomes the just-mentioned problems associated with prior art endodontic procedure.

A more specific object of the invention is to provide such a holder which can be worn by a dentist, and which is usable for dispensing and receiving endodontic files.

Another object of the invention is to provide such a holder which has a sterile file-holding cushion which can be inserted releasably into the holder without compromising cushion sterility.

A further object of the invention is to provide such a holder which can be worn on a user's hand, without appreciably limiting use of that hand.

Still another object of the invention is to provide, for use with an endodontic file having a depth marker slidably held on the file's shaft, a holder which permits the user, in cooperation with his free hand, to adjust the position of the marker on the file shaft.

The holder, or apparatus, of the present invention includes a double-open-ended socket formed by a socket member, and a band by which the holder is attachable to a user's finger. An elongate cushion is adpated for deformed seating within the socket through travel of the cushion inwardly relative to the upper end of the socket. The cushion is constructed to receive a plurality of endodontic files.

In a preferred embodiment of the invention, the socket is tapered between a larger, upper end and a smaller, lower end. The cushion is similarly tapered to be received within the socket, with an end portion of the cushion projecting through the socket's lower end. When pulled downwardly and then released, the cushion's lower end portion bulges against the socket member, adjacent the socket's lower end, forming a bulge which holds the cushion releasably in the socket.

Further, the preferred embodiment of the apparatus is designed for use with an endodontic file having a depth gauge marker held slidably on the file shaft. A calibrated trough arrangement formed in the socket member is dimensioned to receive the depth marker and file shaft, fixedly and slidably therein, respectively. With a file so held, a user can adjust with his free hand the position of the depth marker on the file's shaft.

These and other objects and features of the present invention will become more fully apparent when the following detailed description of a preferred embodiment of the invention is read in connection with the accompanying drawings, wherein:

FIG. 2 is a smaller-scale perspective view of apparatus constructed according to the present invention;

DETAILED DESCRIPTION OF A PREFERRED EMBODIMENT OF THE INVENTION

Figure 1:
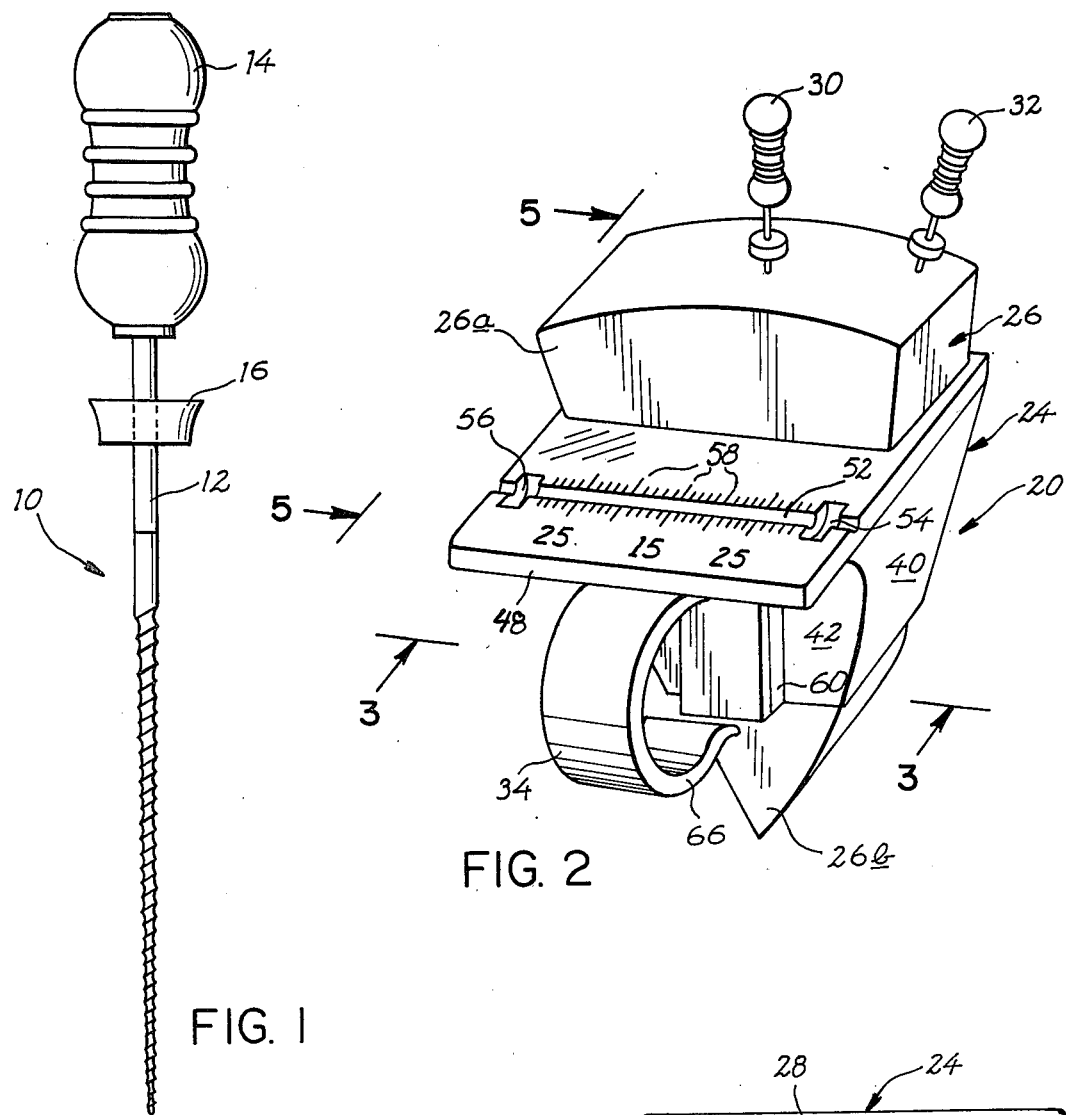
FIG. 1 is an enlarged-scale side view of an endodontic file of a type usable with the present invention.

Looking first at FIG. 1, there is shown generally at 10 an endodontic file of a type designed to be held and dispensed from the apparatus of the present invention. File 10 includes an elongate metal shaft 12 which terminates at its upper end in FIG. 1, in a handle 14 used in handling the file. A depth gauge marker 16 is carried slidably on shaft 12 at a position which is a preselected distance from the file's filing end (the lower end in FIG. 1).

Figure 9:
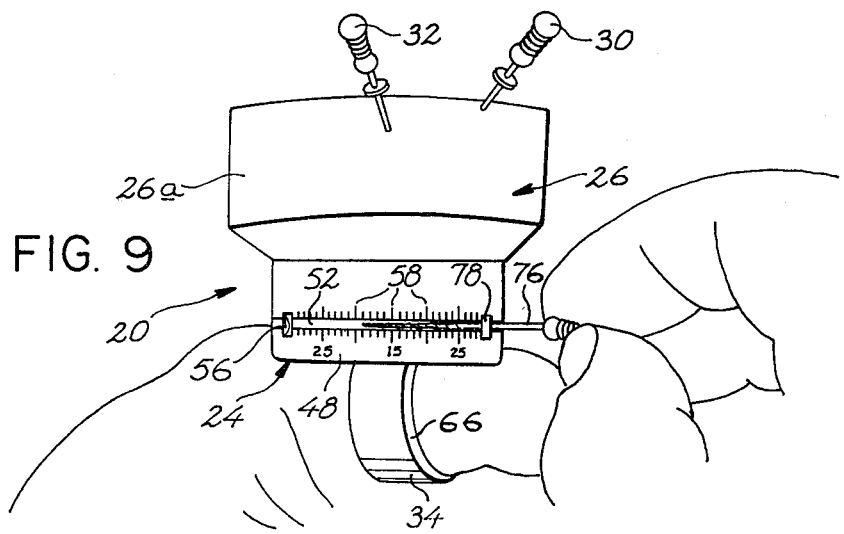
FIG. 9 is a somewhat reduced scale, perspective view of the apparatus as it is intended to be worn and used.

The apparatus of the present invention is illustrated at 20 in FIGS. 2–5, inclusive. Apparatus 20 generally includes a socket-forming member, or means, 24 and a deformable cushion 26 which is seatable releaseably in the socket 28 (FIGS. 3–5) formed by member 24, in a manner to be described. Cushion 26 is adapted to receive and hold, releasably, plural endodontic files, such as files 30, 32, which are similar to above-described file 10. The apparatus is wearable on a user's finger, as shown in FIG. 9, by a band 34, or holding means, which is releasably secured to member 24.

Considering now details of the invention, member 24 is unitary, and is formed of four side walls 36, 38, 40 and 42. Progressing downwardly in socket 28, walls 36, 40 converge at an angle of about 40-degrees, and walls 38, 42 converge at a much smaller angle of about 3-degrees. Thus socket 28 as defined by these walls has a generally inverted, truncated pyrimidal shape, with the cross-sectional area of the socket decreasing continuously from the socket's upper open end 44 to its open lower end 46.

Plural projections, such as projections 37 (FIGS. 3 and 4), are formed on the inner upper surfaces of walls 36, 40—preferably integrally therewith. These projections help to maintain the cushion within the socket as will be considered further below.

Member 24 additionally includes a shelf 48 projecting from the upper end of the member laterally outwardly from wall 42. Wall 42 flares outwardly, toward its upper end to form a gusset 50 which underlies and supports shelf 48. Preferably member 24, including the four side walls, shelf 48 and gusset 50 are formed of molded aluminum or plastic.

Formed in the upper surface of shelf 48 is an elongate slot 52 which extends between the shelf's opposite ends. The slot is dimensioned to receive a portion of a file shaft, such as shaft 12, slidably therein. A pair of sockets 54, 56 are formed adjacent opposed ends of the slot as shown, and are dimensioned to receive snugly therein portions of a gauge marker, such as marker 16 in file 10. Slot 52 and sockets 54, 56 are referred to herein collectively as trough means. The purpose of the slot 52 and sockets will be described shortly.

Displayed along slot 52, on the top of shelf 48, is a plurality of markings, such as markings 58, representing millimeter distance units from sockets 54 and 56. The numerical designations for these markings are symmetric with respect to the two sockets, for reasons to be described.

Figure 3:
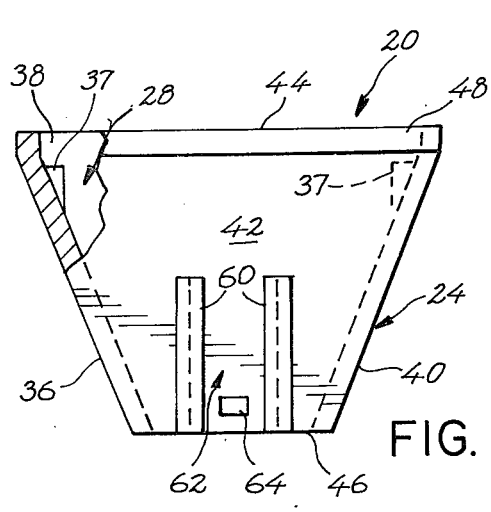
FIG. 3 is a side, partially cutaway view alone of a socket forming member in the apparatus of FIG. 2, taken generally along line 3—3 in FIG. 2.
Figure 4:
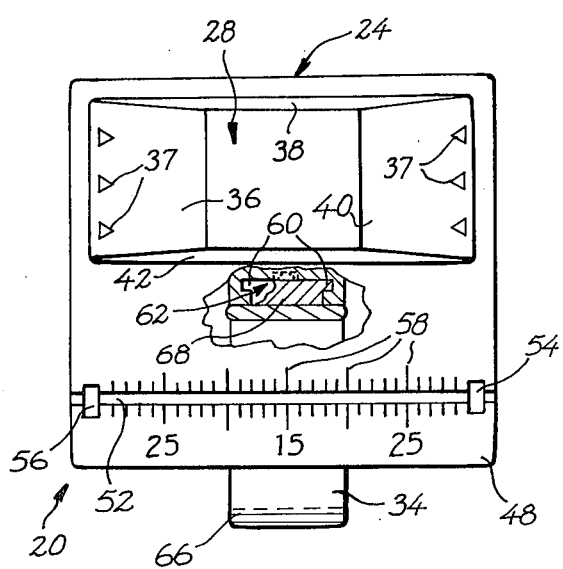
FIG. 4 is a top, partially cutaway view of the apparatus of FIG. 2, with the cushion thereof removed.

Completing the description of member 24, two track members 60 are joined to the lower, central outside portion of wall 42, as seen best in FIG. 3. Each of these members is L-shaped in cross section, as seen in FIG. 4, with the free ends of the two members facing each other to form, on wall 42, a substantially T-shaped track 62. Track 62 and an indentation 64 (see FIG. 3) formed in wall 42 cooperate, in a manner to be considered below, to mount band 34 on member 24.

Figure 5:
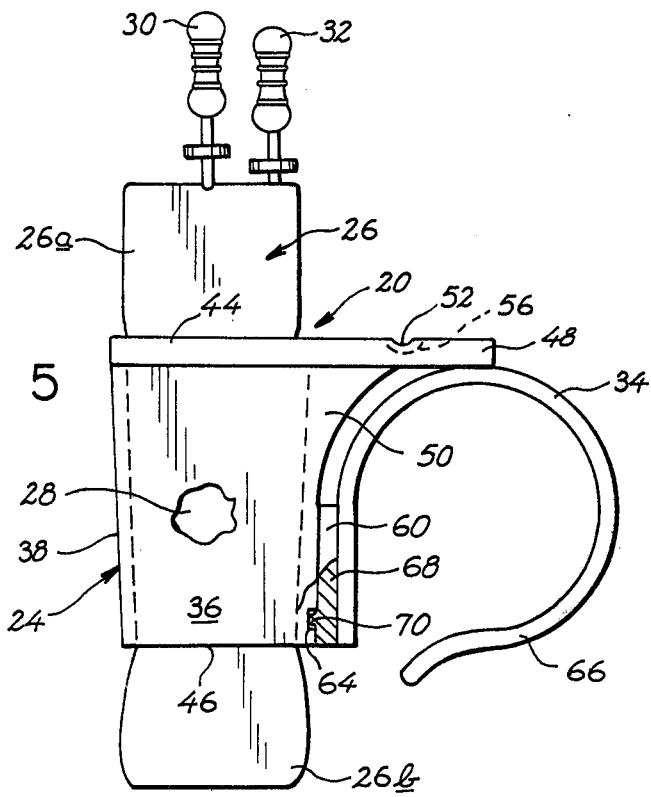
FIG. 5 is a side view of the apparatus taken generally along line 5—5 in FIG. 2.

Band 34 is representative of one of a variety of different-sized finger-bands which may be attached to member 24 to provide a desired-sized finger ring for the apparatus. Band 34 includes a flexible finger-encompassing loop 66, seen best in FIG. 5, and integrally therewith a track-engaging slide 68 which has the generally T-shaped cross section seen in FIG. 4. Slide 68 is dimensioned to be received snugly in track 62. A projection 70 (FIG. 5) formed on slide 68, at the lower portion thereof in FIG. 5, is received within indentation 64 when the band is properly positioned on member 24, thus to lock the band thereto. Slide 68 in band 34 is also referred to herein as an attachment means.

Cushion 26 is generally pie shaped and is dimensioned to seat snugly within socket 28, with the cushion's upper and lower ends 26a, 26b, respectively, extending beyond the upper and lower ends, respectively, of member 24. The cushion is formed of a sponge-like resilient material adapted to hold, releasably, plural files at the upper end of the cushion, as seen in FIGS. 2, 5 and 9. Cushion 26, also referred to herebelow as cushion means, preferably is supplied in sterile, disposable form.

Figure 7:
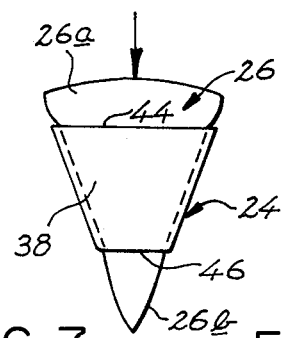
Figure 8:
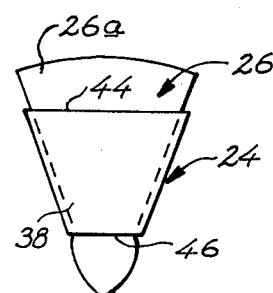

According to an important feature of the present invention, the cushion is deformably stretchable in a top-to-bottom direction as seen particularly with reference to FIG. 7. Such stretching is produced, when the cushion is inserted in socket 28, by pulling downwardly on the lower end region of the cushion, thereby drawing the upper portion of the cushion inwardly with respect to the socket's upper end. Such downward movement of the cushion with respect to the socket's upper end is accommodated in part by a decrease in the side-to-side dimensions in the cushion as the same is stretched in a top-to-bottom direction. Accordingly, when the stretched cushion is released, as in FIG. 8, the cushion's lower end portion 26b tends to resume its normal dimensions, causing the cushion to bulge below the lower end of the socket. This bulge, which is seen from two different sides of the cushion in FIGS. 5 and 8, produces friction locking of the cushion in the socket. Projections 37 also assist in this respect.

Figure 6:
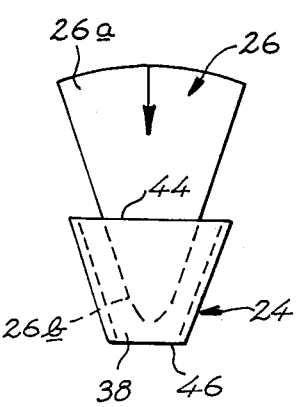
FIGS. 6–8 illustrate schematically and in reduced scale, successive operations used in seating a cushion releasably in the socket-forming member in the apparatus of FIG. 1.

Operation of apparatus 20 in endodontic procedure will now be described. To prepare the apparatus for use, a fresh cushion, such as cushion 26, is placed in the socket, as indicated in FIG. 6. The cushion is then lock-seated releasably in the socket by the above-described manipulation, which includes pulling the cushion's lower end portion downwardly, to pull the cushion inwardly with respect to the socket's upper end, as has been described. When the cushion's lower end portion is released, it bulges against the socket member, adjacent the socket's lower end, as noted above, with the resulting bulge serving to aid in holding the cushion in the socket. It can be appreciated that the just-described placement and friction locking of the cushion in the socket requires handling the cushion at its sides and bottom end region only, without the need or danger of touching, and thereby contaminating, the cushion's upper file-holding surface.

As illustrated in FIG. 9, the apparatus is fitted on a user's finger as a ring, with band 34 encircling such finger. The apparatus so attached is not appreciably more burdensome than a large ring, and does not, therefore, significantly interfere with the dentist's use of that hand.

As noted above, cushion 26 is designed to hold a plurality of files, such as files 30, 32, in positions easily accessible to the dentist during an endodontic procedure. Typically the files held in cushion 26 will have their depth gauge markers preset at desired positions on the associated file shafts. The manner in which the present invention is used by the dentist to preset such file markers is illustrated in FIG. 9. With the apparatus worn as shown—in this case on a finger in the user's left hand the user places a file, such as the file shown at 76, held in his right hand, in slot 52, with the file's depth marker 78 received in socket 54, as shown. The file is now moved axially to a desired marking on shelf 48 to set the file's filing end a desired distance from marker 78. The file is then placed in the cushion for later use during the endodontic procedure. It can be appreciated from the above that if the apparatus were worn on a finger in the user's right hand, the same marker-setting operation could be performed, with the user's free (left) hand, by placing the file's depth marker in socket 56.

As the files are used, during the endodontic procedure, these are replaced in the cushion. At the completion of the endodontic procedure the files are removed from the cushion and suitably prepared for reuse. The cushion is removed forceably from the socket and discarded.

It can now be appreciated how the various objects of the present invention are met. The apparatus provides a convenient, safe way to handle files during an endodontic procedure. Since the file holder is held by the dentist, the risk that the dentist will inadvertently pierce himself with a contaminated file during file transfer is minimized. The device also frees the dentist's assistant for other work.

According to another important object of the present invention, a presterilized, disposable file-holding cushion may be seated releasably in the apparatus' socket by a manipulation which avoids touching the file-holding surface of the cushion, thus avoiding contaminating this surface. Finally, the apparatus of the present invention provides a depth-setting slot by which the endodontist, with the apparatus worn on either hand, may make a selected adjustment of a depth marker position on a file.

While a preferred embodiment of the present invention has been described hereabove, it is obvious that various changes and modifications may be made without departing from the spirit of the invention.

It is claimed and desired to secure by Letters Patent:

1. Finger ring apparatus for use in holding an endodontic file and the like, comprising means defining an elongated double-open-ended socket, elongated, resiliently deformable cushion means constructed to receive, releasably and at one of its ends, such a file which is inserted into said cushion means, said cushion means being adapted for deformed seating within said socket through travel of the cushion means inwardly relative to one end of the socket as a result of manipulation of that end of said cushion means which is opposite its said one end which extends through the outer socket end, deformation of said cushion means with seating thereof producing friction locking between the cushion means and said socket, and holding means joined to said socket-defining means constructed to be held by a user's hand.

2. The apparatus of claim 1, wherein said one end of said socket has a larger cross-sectional area than the other end of the socket.

3. The apparatus of claim 2, wherein said socket takes the form generally of an inverted truncated pyramid.

4. The apparatus of claim 2, wherein, with said cushion means seated in said socket, said opposite end of said cushion means projects beyond said other end of said socket, and includes a portion which bulges laterally relative to said means defining said socket.

5. The apparatus of claim 1 wherein said holding means includes means accommodating releasable attachment of the holding means and said socket-defining means.

6. Finger ring apparatus for use in holding an endodontic file having a shaft and a depth marker held slidably thereon, said apparatus comprising means defining an elongated double-open-ended socket, trough means on said socket-defining means for receiving such a marker and shaft fixedly and slidably therein, respectively, elongated, resiliently deformable cushion means constructed to receive, releasably and at one of its ends, such a file, said cushion means being adapted for deformed removable captured seating within said socket through travel of the cushion means inwardly relative to one end of the socket as a result of manipulation of that end of said cushion means which is opposite its said one end, deformation of said cushion means with seating thereof producing friction locking between the cushion means and said socket, and holding means joined to said socket-defining means constructed to be held by a user's hand.

* * * * *